US007856134B2

(12) United States Patent
Rührnschopf et al.

(10) Patent No.: US 7,856,134 B2
(45) Date of Patent: Dec. 21, 2010

(54) METHOD FOR GENERATING IMAGE DATA RELATING TO A VIRTUALLY PRESCRIBABLE X-RAY TUBE VOLTAGE FROM FIRST AND SECOND CT IMAGE DATA

(75) Inventors: Ernst-Peter Rührnschopf, Erlangen (DE); Martin Sedlmair, Markt Schwaben (DE); Karl Stierstorfer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 12/457,973

(22) Filed: Jun. 26, 2009

(65) Prior Publication Data

US 2010/0014737 A1 Jan. 21, 2010

(30) Foreign Application Priority Data

Jun. 27, 2008 (DE) ................ 10 2008 030 552

(51) Int. Cl.
*G06K 9/00* (2006.01)
(52) U.S. Cl. ...................... 382/131; 382/128
(58) Field of Classification Search ................ 382/100, 382/128, 131
See application file for complete search history.

(56) References Cited

U.S. PATENT DOCUMENTS

| 4,247,774 A | 1/1981 | Brooks |
| 4,991,190 A | 2/1991 | Mori |

(Continued)

FOREIGN PATENT DOCUMENTS

DE 10302565 A1 8/2004

(Continued)

OTHER PUBLICATIONS

Peter M. Joseph and Robin D. Spital; A Method for Correcting Bone Induced Artifacts in Computed Tomography Scanners Joseph et al.; J. Comp. Assist. Tomogr., Jan. 1978, vol. 2, pp. 100-108; Magazine; 1978.

(Continued)

*Primary Examiner*—Bhavesh M Mehta
*Assistant Examiner*—Stephen R Koziol
(74) *Attorney, Agent, or Firm*—Harness, Dickey & Pierce, P.L.C.

(57) ABSTRACT

A method for generating image data relating to a virtually prescribable X-ray tube voltage $U_3$ from first and second dual energy CT image data is disclosed. In at least one embodiment, the method includes providing the first and second CT image data; prescribing the virtual X-ray tube voltage $U_3$ with $U_3 \neq U_1$ and $U_3 \neq U_2$, on the basis of the first and second CT image data for two prescribable base materials A, B; determining in each case a spatial density distribution $\rho_A(x), \rho_B(x)$, assigned to the base materials A, B, in the reconstructed object volume, $\rho(x)=\rho_A(x)+\rho_B(x)$ holds true for a density $\rho(x)$ of a voxel x in the reconstructed object volume; providing an effective mass attenuation coefficient $<\alpha_A>_{U_3}$ for the base material A, and an effective mass attenuation coefficient $<\alpha_B>_{U_3}$ for the base material B, the effective mass attenuation coefficients $<\alpha_A>_{U_3}$ and $<\alpha_B>_{U_3}$ respectively being valid for an X-ray spectrum $S(E, U_3)$ assigned to the virtual X-ray tube voltage $U_3$; and determining the image data as a third distribution of linear attenuation coefficients $\mu_3(x)$ in the reconstructed object volume on the basis of the following relationship: $\mu_3(x)=<\alpha_A>_{U_3}\cdot\rho_A(x)+<\alpha_B>_{U_3}\cdot\rho_B(x)$.

20 Claims, 1 Drawing Sheet

U.S. PATENT DOCUMENTS

| | | | |
|---|---|---|---|
| 7,457,450 B2 * | 11/2008 | Bruder et al. | 382/130 |
| 7,477,765 B2 * | 1/2009 | Heismann | 382/128 |
| 7,643,663 B2 * | 1/2010 | Wiemker et al. | 382/131 |
| 2004/0223585 A1 | 11/2004 | Heismann et al. | |
| 2005/0084069 A1 | 4/2005 | Du | |
| 2005/0089134 A1 | 4/2005 | Bruder et al. | |
| 2006/0109949 A1 | 5/2006 | Du et al. | |
| 2008/0219532 A1 * | 9/2008 | Hopkins et al. | 382/131 |
| 2009/0052612 A1 | 2/2009 | Leblanc et al. | |
| 2009/0080597 A1 * | 3/2009 | Basu | 378/5 |

FOREIGN PATENT DOCUMENTS

DE            10143131 B4     3/2006

OTHER PUBLICATIONS

B. J. Heismann et al.; "Density and atomic number measurements with spectral x-ray attenuation method", Journal of Applied Physics, vol. 94, No. 3, 2003, pp. 2073-2079; Magazine.

H. Aichinger, J. Dierker, S. Joite-Barfuss, M. Säbel; Radiation Exposure and Image Quality in X-Ray Diagnostic Aichinger et al.; Radiology, Springer Verlag, Berlin 2004, pp. 123-129; Others; 2004.

M. Zellerhoff, B. Scholz, E.-P. Rührnschopf, T. Brunner; "Low contrast 3D reconstruction from C-arm data", Proceedings of SPIE, Medical Imaging 2005, vol. 5745, pp. 646-655; Magazine; 2005.

Peter M. Joseph, Christopher Ruth; A Method for Simultaneous Correction of Spectrum Hardening Artifacts in CT Images containing both Bone and Iodine Joseph, Ruth; Med Phys. Oct. 1997; 24(10), pp. 629-634.; Magazine; 1997.

Kyriakou et al.; Combining deterministic and Monte Carlo calculations for fast estimation of scatter intensities in CT, Phys. Med. Biol. 51 (2006), pp. 4567-4586; ICMP 2005; Others; 2005.

Robert E. Alvarez and A. Macovski; Energy-selective reconstructions in X-ray computerised tomography Alvarez et al.; Phys. Med. Biol. 21. pp. 733-744; Others; 1976.

Johnson, Thorsten R.C. et al., "Material differentiation by dual energy CT: initial experience", European Radiology Online, Bd. 17, No. 6, Dec. 2006, pp. 1510-1517, XP002497949; Others.

NIST (National Institute of Standards and Technology); X-Ray Mass Attenuation Coefficients; http://physics.nist.gov/PhysRefData/XrayMassCoef/tab3.html; Others, retrieved Jun. 2, 2009.

* cited by examiner

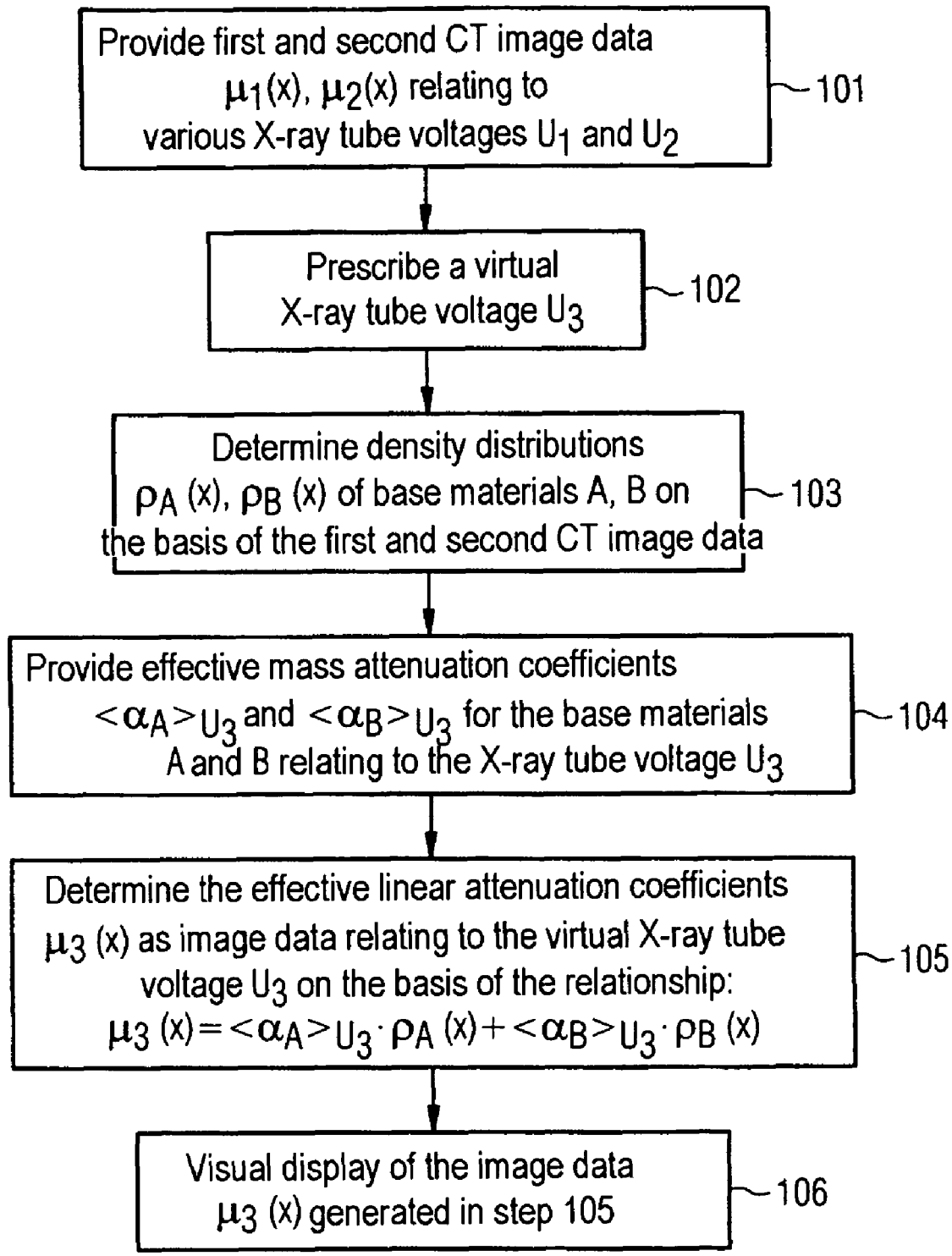

US 7,856,134 B2

METHOD FOR GENERATING IMAGE DATA RELATING TO A VIRTUALLY PRESCRIBABLE X-RAY TUBE VOLTAGE FROM FIRST AND SECOND CT IMAGE DATA

PRIORITY STATEMENT

The present application hereby claims priority under 35 U.S.C. §119 on German patent application number DE 10 2008 030 552.9 filed Jun. 27, 2008, the entire contents of which are hereby incorporated herein by reference.

FIELD

At least one embodiment of the present invention occurs in the field of medical technology and generally relates to a method for generating image data relating to a virtually prescribable X-ray tube voltage from first and second CT image data. In at least one embodiment, the first and second CT image data have been obtained by way of a computer tomograph by simultaneously or nearly simultaneously recording an object volume, the first CT image data describe a first distribution of the linear attenuation coefficient $\mu_1(x)$ for a first X-ray spectrum $S_1$, and the second CT image data describe a second distribution of the linear attenuation coefficient $\mu_2(x)$ for a second X-ray spectrum $S_2$, each voxel x of an object volume which is reconstructed from the first and second CT image data respectively being assigned the linear attenuation coefficients $\mu_1(x)$ and $\mu_2(x)$, and the first X-ray spectrum $S_1$ is assigned to a first X-ray tube voltage $U_1$, and the second X-ray spectrum $S_2$ is assigned to a second X-ray tube voltage $U_2$, in which case $U_1 \neq U_2$.

BACKGROUND

The result of radiographic methods such as for example, computed tomography, mammography, angiography, X-ray inspection technology or comparable methods is, firstly, the display of the attenuation of an X-ray beam along its path from the X-ray source to the X-ray detector in a projection image. This attenuation is caused by the irradiated materials along the beam path, and so the attenuation can also be understood as a line integral over the attenuation coefficients of all the volume elements (voxels) along the beam path. Particularly in the case of tomography methods, for example in X-ray computed tomography (CT), it is possible to use reconstruction methods to calculate backward from the projected attenuation data to the attenuation coefficients $\mu(x)$ of the individual voxels x, and thus to arrive at a substantially more sensitive examination than with a consideration purely of projection images.

In order to display the attenuation distribution, the typical approach is generally to replace the physical linear attenuation coefficient $\mu(x)$ by the use of a value normalized to the attenuation coefficient of water, the so-called CT value. This is calculated from a linear attenuation coefficient $\mu(x)$ currently determined by measurement, and the reference attenuation coefficient $\mu_{H2O}$, using the following equation:

$$C = \frac{\mu(x)}{\mu_{H2O}} - 1000,$$

with the CT number C in Hounsfield Units [HU]. A value of $C_{H2O}=0$ HU is returned for water, and a value of $C_L=-1000$ HU is returned for air. Since the two displays can be transformed into one another or are equivalent, the term attenuation value generally selected below denotes both the linear attenuation coefficient $\mu(x)$ and an attenuation value dependent linearly thereon such as, for example, the CT value.

Modern tomography devices, such as, for example, X-ray computed tomography devices or C-arc units, are used for the recording and evaluation of image data in order to display the three-dimensional attenuation distribution. X-ray computed tomography devices generally have a recording system with an X-ray tube and a detector, lying opposite the latter, for detecting the radiation emanating from the X-ray tube and irradiating the object. The recording system rotates during the recording once or several times about the examination object. C-arc units, which are frequently used for imaging during surgical operations, comprise or two so-called C-arc systems as recording systems that are respectively rotated during the image data recording by an angle $\geq 180°$ about the object to be examined. The measured data supplied by the recording systems are further processed in an evaluation unit in order to obtain the desired sectional image or volume image of the examination area.

U.S. Pat. No. 4,991,190 A has also disclosed an X-ray computed tomography unit that has a number of recording systems that can revolve about a common rotation axis. The advantage of such tomography units with a number of recording systems as against a unit with only one recording system resides in the elevated data recording rate, which leads to a shorter recording time and/or an increased temporal resolution. A shortened recording time is advantageous because, in the reconstructed image, this results in the minimization of movement artifacts that can be caused, for example, by movement of the patient or of his organs such as, for example, the heart during the image data recording. An increased temporal resolution is required, for example, in order to display movement sequences when the data used for the reconstruction of an image need to be recorded in the shortest possible time. An imaging tomography unit with at least two recording systems is, for example, also disclosed in DE 103 02 565.

However, it is not possible to infer the material composition of an examination object from the attenuation value distribution of such X-ray recordings, since the X-ray absorption is determined both by the effective atomic number of the material and by the material density. Consequently, materials or tissue of different chemical as well as physical composition can exhibit identical attenuation values in the X-ray images.

In order to enhance the informativeness of an X-ray image based on the local attenuation coefficient, it is therefore known, for example from U.S. Pat. No. 4,247,774 A, to make use of X-ray spectra or X-ray quantum energies that differ from one another in order to generate an X-ray image. This method used in the field of computed tomography, which is also generally denoted as duel energy CT, makes use of the fact that materials of higher atomic number absorb low energy X-radiation substantially more strongly than materials of lower atomic number. In the case of higher X-ray energies, the attenuation values therefore match one another and are predominantly a function of the material density. By calculating the differences in the X-ray images recorded for different X-ray tube voltages, it is therefore possible to obtain additional information about the materials on which the individual image areas are based.

Even more specific statements are obtained when, in addition, the method of so-called base material decomposition is applied during X-ray imaging. In this method, the X-ray attenuation values of an examination object are measured with X-ray beams of lower and higher energy, and the values obtained are compared with the corresponding reference values of two base materials such as, for example, calcium for bone mineral (hydroxylapatite), and water for soft part tissues. It is assumed in this case that each measured value may be represented as a linear superposition of the measured values of the two base materials. Thus, a bone component and a soft tissue component can be calculated for each element of the pictorial display of the examination object from the comparison of the values of the base materials, such that it is then possible to transform the original recordings into displays of the two base materials.

Furthermore, the publication DE 101 43 131 B4 discloses a method that can be used to calculate the spatial distribution of the density $\rho(r)$ and the effective atomic number $Z(r)$ by evaluating the spectrally influenced measured data of an X-ray apparatus. The method is denoted as $\rho$-Z decomposition.

The evaluation of CT image data, recorded with the aid of two X-ray tube voltages, by means of photo/Compton effect decomposition, that is to say a decomposition by components of the photo effect and components of the Compton effect is known, for example, from the publication: Robert E. Alvarez and A Macovski, "Energy-selective Reconstruction in X-ray Computerized Tomography", PHYS. MED. BIOL., 1976, vol. 21, No. 5, 733-744.

The recording of the CT image data with different spectral distributions that is required in the case of the three decomposition methods addressed is effected, for example, by operating the X-ray source of the recording system alternately with different tube voltages, or by providing two X-ray tubes that are operated synchronously with different tube voltages. The decomposition methods addressed can be used to identify different materials (for example soft part tissues, bone, contrast agent), and specifically reconstruct their spatial density distributions.

In the case of dual energy CT recordings, independent measurements are present in initial data records in conjunction with different X-ray tube voltages. For each voxel they supply two equations for two unknown parameters with the aid of which it is possible to characterize chemical material differences, for example.

For the further discussions,

Method 1: is understood as the base material decomposition, that is to say decomposition by components of two prescribable base materials (for example, plexiglass/aluminum; soft part/bone, water/iodine, etc.), Method 2: is understood as the photo/Compton effect decomposition, that is to say decomposition by components of the photo effect and of the Compton effect on the linear attenuation coefficient, and Method 3: is understood as the $\rho$-Z decomposition, that is to say representation of the density and the effective atomic number.

The best known methods are Methods 1 and 2, the base material decomposition being that most frequently applied owing to its graphic quality. Methods 1 and 2 lead to linear equations. Method 3 leads to nonlinear equations (compare in this regard B. J. Heismann et al., "Density and atomic number measurements with spectral X-ray absorption methods", J. Applied Physics, Vol. 94(3), 2073-2079, (2003)). However, compared with Method 1 it has the advantage that it does not require any arbitrary advance stipulation of base materials. Said three methods are quantitative imaging methods. However, they can also be simplified to produce qualitative material classification. In this case, parameters derived from the measurements are used in order to assign the voxels of the image volume to various material classes.

The presence of two CT image data records in accordance with the two different X-ray tube voltages, yields a multiplicity of options for processing and visualization that support the posing of diagnostic questions. Apart from the dual energy material decomposition itself, every CT image recorded with the aid of different X-ray tube voltages is available.

The X-ray tube voltages in the case of dual energy imaging, for example at 80 kV and 140 kV, typically deviate substantially from the X-ray tube voltage of approximately 120 kV that is customary in the case of standard CT pictures. As a consequence thereof, the image impressions of visualized dual energy CT pictures likewise deviate, for example with regard to contrast and spatial resolution, from the image impression that is customary from standard CT pictures. On the part of the doctors who are accustomed to standard CT pictures, there is now a need to visualize dual energy CT image data in a customary form, that is to say in accordance with the X-ray tube voltage that is usual for standard CT pictures.

SUMMARY

In at least one embodiment of the present invention, a method is specified with the aid of which it is possible, starting from dual energy CT image data that have been recorded with the aid of two different energy spectra or two appropriate X-ray tube voltages, to determine image data relating to a prescribable third, virtual X-ray tube voltage. A particular aim in this process is, in particular, to consider nonlinear dependencies of the linear attenuation coefficients or of the CT values on the associated X-ray tube voltages. It is also intended to be possible for a viewer to visualize the determined image data, in particular to provide the image impression of a standard CT picture.

According to at least one embodiment of the invention, the method for generating image data relating to a virtually prescribable X-ray tube voltage $U_3$ from first and second CT image data, wherein the first and second CT image data have been obtained by way of a computer tomograph by simultaneously, or nearly simultaneously, recording an object volume, the first CT image data describe a first distribution of the linear attenuation coefficient $\mu_1(x)$, or an attenuation value linearly dependent thereon, for a first X-ray spectrum $S_1$, and the second CT image data describe a second distribution of the linear attenuation coefficient $\mu_2(x)$, or an attenuation value $C_{1,2}(x)$ linearly dependent thereon, for a second X-ray spectrum $S_2$, each voxel x of an object volume which is reconstructed from the first and second CT image data respectively being assigned the linear attenuation coefficients $\mu_1(x)$ and $\mu_2(x)$, or corresponding attenuation values $C_{1,2}(x)$ and the first X-ray spectrum $S_1$ is assigned to a first X-ray tube voltage $U_1$, and the second X-ray spectrum $S_2$ is assigned to a second X-ray tube voltage $U_2$, in which case $U_1 \neq U_2$, comprises the following steps:

a) providing the first and second CT image data,
b) prescribing the virtual X-ray tube voltage $U_3$, where $U_3 \neq U_1$ and $U_3 \neq U_2$,
c) using the first and second CT image data for two prescribable base materials A, B to determine in each case a spatial density distribution $\rho_A(x)$, $\rho_B(x)$ assigned to the base materials A, B, in the reconstructed object volume, $\rho(x)=\rho_A(x)+\rho_B(x)$ holding true for a density $\rho(x)$ of a voxel x in the reconstructed object volume,
d) providing an effective mass attenuation coefficient $<\alpha_A>_{U_3}$ for the base material A, and an effective mass attenuation coefficient $<\alpha_B>_{U_3}$ for the base material B, the effective mass attenuation coefficients $<\alpha_A>_{U_3}$ and $<\alpha_B>_{U_3}$ respectively being valid for an X-ray spectrum $E_3$ assigned to the virtual X-ray tube voltage $U_3$, e) determining the image data as a third distribution of effective linear attenuation coefficients $\mu_3(x)$ in the reconstructed object volume in relation to the voltage $U_3$ on the basis of the following relationship:

$\mu_3(x)=<\alpha_A>_{U_3}\cdot\rho_A(x)+<\alpha_B>_{U_3}\cdot\rho_B(x)$.

At least one embodiment of the present application is based on Method 1, that is to say on the method of base material decomposition. The idea on which the invention is based can, however, be applied in principle to any of the three decomposition methods 1 to 3 described in the introduction. Since the decomposition by base materials (Method 1) is, however, the most frequently applied dual energy decomposition method, the following descriptions concentrate on this method. The necessary modifications for the application of the inventive idea to the two other decomposition methods advanced above (Methods 2 and 3) is likewise described further below.

The inventive method of least one embodiment proceeds from the fact that the X-ray attenuation values (attenuation values/CT values/linear attenuation coefficients) in the first and second CT image data, that is to say in the first and second CT image data provided in step a), are present as corrected and calibrated data, or correspond to the physical attenuation coefficient or a value linearly dependent thereon. Scattered radiation correction may be mentioned as an example of data corrections that may be required. In step b), the virtual X-ray tube voltage $U_3$ is preferably selected in such a way that $U_3$ lies between $U_1$ and $U_2$. In a particularly preferred design variant of the inventive method, a voltage of approximately 120 kV is selected as X-ray tube voltage $U_3$.

The following statements serve the purpose of further explaining the inventive subject matter of at least one embodiment and advantageous method variants. The following designations and definitions are decisive in this case.

x spatial coordinate of a voxel in the reconstructed object volume;

$\mu$ linear attenuation coefficient [cm$^{-1}$];

$\alpha=\mu/\rho$ mass attenuation coefficient [cm$^2$/g];

$\rho$ density [g/cm$^3$];

$\mu_1$ effective linear attenuation coefficient relating to the first X-ray tube voltage $U_1$;

$\mu_2$ effective linear attenuation coefficient relating to the second X-ray tube voltage $U_2$;

$\mu_{k,W}$ effective linear attenuation coefficient for water for the X-ray tube voltage $U_1$ or $U_2$, respectively, (k=1 or k=2)

$\Delta\mu_k=\mu_k-\mu_{k,W}$ difference of the effective linear attenuation coefficient relating to water for the X-ray tube voltage $U_1$ and $U_2$, respectively, (k=1 or k=2).

In this description, "effective linear attenuation coefficient" is to be understood as the averaging of the linear attenuation coefficient $\mu$ over the photon energy spectrum E corresponding to a tube voltage U, with additional consideration of spectral filters and the energy dependent response characteristic of the detector. The averaging is symbolized by angle brackets:

$$\mu_1 = <\mu>_{U_1} \tag{1a}$$

$$\mu_2 = <\mu>_{U_2} \tag{1b}$$

$$C_k = \frac{\mu_k}{\mu_{k,W}} = \frac{\mu_k}{\mu_{k,W}} - 1; k = 1, 2 \tag{2}$$

denotes a local CT value, that is to say a CT value assigned to each voxel x in the two reconstructed dual energy CT pictures. Apart from the factor 1000, this is the usual display in CT images in HU units (Hounsfield units).

Furthermore, the averaging symbolized by angle brackets in equations 1a, 1b is defined as follows: Let g(E) be a function dependent on the photon energy E, in particular the linear attenuation coefficient dependent on the photon energy ($g=\mu(E)$) or the mass attenuation coefficient ($g=\alpha(E)=\mu(E)/\rho$), and then let $$<g>_U \int_0^{eU} g(E)S(E,U)dE. \tag{3a}$$

The associated probability distribution density function $$S(E,U) = \frac{F(E)Q(E)D(E)e^{-\mu_0(E)t}}{\int_0^{eU} F(E)Q(E)D(E)e^{-\mu_0(E)t}dE} \tag{3b}$$

is normalized such that its integral=1. The upper integration bound in equations 3a and 3b is given by the maximum energy eU (e=charge of an electron) of the quanta from the anode of the X-ray tubes operated with the aid of the acceleration voltage U. In equation (3b), F(E) denotes the transparency of spectral filters that may be used, Q(E) denotes the energy dependent emission photon spectrum of the X-ray tubes, and D(E) denotes the response sensitivity of the X-ray detector used.

In the case of CT recordings, the X-ray measuring beams penetrating the patient from various directions generally experience different attenuations and therefore a different spectral hardening. If this hardening is not corrected, typical image disturbances (hardening artifacts) result. The exponential term in equation (3b) represents in this case an overall consideration of the hardening of the spectrum in the passage of the radiation through the examination object (patient, for example). In this case, $\mu_0$ corresponds to a mean attenuation coefficient, and t corresponds to a mean material thickness. Deviations relating to this "standard spectrum" in equation (3b) can be corrected with the aid of known correction algorithms for beam hardening. Such methods may be found, for example, in the publications P. Joseph et al., "A Method for Correcting Bone Induced Artifacts in Computed Tomography Scanners", J. Comp. Assist. Tomogr., January 1978, Vol. 2 100-108; or P. Joseph et al., "A Method for Simultaneous Correction of Spectrum Hardening Artifacts in CT Images Containing both Bone and Iodine", Med. Phys., Vol 24(10), October 1997, 1629-34, the entire contents of each of which are hereby incorporated herein by reference.

In an advantageous variant of at least one embodiment of the inventive method, the effective mass attenuation coefficients $<\alpha_A>_U$ and $<\alpha_B>_U$ for arbitrary base materials A, B, and an X-ray spectrum E assigned to an arbitrary X-ray tube voltage U, in particular $U=U_1$, $U=U_2$, $U=U_3$, are therefore determined via the following relationships:

$$<\alpha_{A,B}>_U = \int_0^{eU} \alpha_{A,B}(E)S(E,U)dE,$$

wherein

-continued $$S(E, U) = \frac{F(E)Q(E)D(E)e^{-\mu_0(E)t}}{\int_0^{eU} F(E)Q(E)D(E)e^{-\mu_0(E)t} dE},$$

where:

S(E,U) is a probability distribution density function normalized to 1,

U is the X-ray tube voltage, e is the elementary charge of an electron,

E is energy,

F(E) is the transparency of spectral filters which are present, which is dependent on the energy E, Q(E) is the energy-dependent emission photon spectrum of the X-ray tubes, D(E) is the response sensitivity, dependent on the energy E, of an X-ray detector, $\mu_0$ is the mean attenuation coefficient of the base material A and B, respectively, t is the mean material thickness of the base material A and B, respectively.

As described in the introduction, so-called material images can be generated for all voxels x of the reconstructed object volume by means of the first and second CT image data (relating to the X-ray tube voltage $U_1$ and $U_2$, respectively) recorded using the dual energy method. It may now be assumed that a preclassification has already been carried out in the reconstructed object volume, that is to say that partial volume areas have been identified as belonging to material classes $M_i$ in accordance with the material composition of their voxels, the index i specifying the ith material class. It is thereby possible to perform a voxelwise assignment to the material classes $M_i$ in the reconstructed object space, and thus, for example, to identify soft part tissues, calcification or contrast agent mixtures, etc. Each material class $M_i$ can for its part consist of 2 base components (substances), for example a contrast agent mixture of iodine and blood (or water), calcification from bone mineral (hydroxylapatite) and a non-calcareous base substance (for example, connective tissues or cartilage), etc. It can also happen in a special case that a material class $M_i$ is described by only a single base component. The general case in which a material class $M_i$ is respectively defined by two base materials is described below. In the case of only one base material, the formulae are correspondingly simplified.

In a further advantageous method variant, a number N of different material classes $M_i$ (i=1, ..., N) is therefore defined, each material class $M_i$ being determined by a prescribable combination of two base materials $A_i$ and $B_i$ characterizing the material class $M_i$. The assignment of the voxels x in the reconstructed object volume to the individual material classes can be performed by segmentation and/or classification algorithms.

A voxel that belongs to an arbitrary material class $M_i$ may now be considered. The two base material components may be indicated as $A_i$, $B_i$. Let $\rho(x)$ be the physical density of the material in a voxel x, and let $\rho_{A_i}(x)$ and $\rho_{B_i}(x)$, respectively, be the partial densities of the two base components $A_i$ and $B_i$, where $\rho(x)=\rho_{A_i}(x)+\rho_{B_i}(x)$. The identifications for the voxel x and for the material class $M_i$ are initially left out below for the purpose of simplifying the notation. Furthermore, linear attenuation coefficients $\mu(x)$ are considered instead of the CT values.

The following equations hold true:

$$\mu_1 = <\alpha_A>_{U_1} \cdot \rho_A + <\alpha_B>_{U_1} \cdot \rho_B \quad (4a)$$

$$\mu_2 = <\alpha_A>_{U_2} \cdot \rho_A + <\alpha_B>_{U_2} \cdot \rho_B, \quad (4b)$$

where $\mu_{1,2}$ is the effective linear attenuation coefficient relating to the first or second X-ray tube voltage $U_1$ and $U_2$, respectively;

$<\alpha_A>_{U_{1,2}}$, $<\alpha_B>_{U_{1,2}}$ is the effective mass attenuation coefficient for the base material A or B, respectively, in relation to the X-ray tube voltage $U_1$ or $U_2$; and $\rho_A$, $\rho_B$ are the partial densities of the base materials A, B.

In principle, the effective mass attenuation coefficients can be calculated in advance in accordance with equations (3a) and (3b) for each base material and for each voltage for which the tube spectrum is known. Tabulated attenuation coefficients for all elements and for chemical compounds and biological tissue are to be found, for example, in the data collection of the National Institute of Standards and Technology (NIST) (http://physics.nist.gov/PhysRefData/XrayMassCoef/tab3.html). Energy spectra for X-ray tubes are published, for example, in A. Aichinger et al., "Radiation Exposure and Image Quality in X-Ray Diagnostic Radiology", Springer-Verlag 2004, Part IV, Supplement iV.1 X-ray Spectra, 123-130, the entire contents of which are hereby incorporated herein by reference. The weights:

$$\alpha_{11} = <\alpha_A>_{U_1}, \alpha_{12} = <\alpha_B>_{U_1} \quad (5a)$$

$$\alpha_{21} = <\alpha_A>_{U_2}, \alpha_{22} = <\alpha_B>_{U_2} \quad (5b)$$

in the above system of equations (4a), (4b) can therefore be taken as known. If the matrix:

$$H = \begin{pmatrix} \alpha_{11} & \alpha_{12} \\ \alpha_{21} & \alpha_{22} \end{pmatrix}, \quad (6)$$

and the vectors $$\hat{\mu} = \begin{pmatrix} \mu_1 \\ \mu_2 \end{pmatrix}, \quad (7)$$

and $$\hat{\rho} = \begin{pmatrix} \rho_A \\ \rho_B \end{pmatrix} \quad (8)$$

are introduced, the physical densities $\rho_1(x)$ and $\rho_2(x)$, respectively, of the two base materials result by matrix inversion from the measured linear attenuation values $\mu_1(x)$ and $\mu_2(x)$ as $$\hat{\rho} = H^{-1} \cdot \hat{\mu}. \quad (9)$$

It is thereby possible for volume images of the density distributions of various body tissues and base materials to be generated from the first and second CT image data.

Consequently, in step c) for determining the spatial density distribution $\rho_A(x)$, $\rho_B(x)$ assigned to the base materials A, B, effective mass attenuation coefficients $<\alpha_A>_{U_1}$, $<\alpha_A>_{U_2}$ are firstly advantageously determined or provided for the base material A, and $<\alpha_B>_{U_1}$, $<\alpha_B>_{U_2}$ are determined or provided for the base material B, the mass attenuation coefficients $<\alpha_A>_{U_1}$, and $<\alpha_B>_{U_1}$ being valid respectively for the X-ray spectrum $S(E,U_1)$ assigned to the first X-ray tube voltage $U_1$, and the mass attenuation coefficients $<\alpha_A>_{U_2}$, and $<\alpha_B>_{U_2}$ respectively being valid for the X-ray spectrum $S_2(E,U_2)$ assigned to the second X-ray tube voltage $U_2$. The density distributions $\rho_A(x)$ and $\rho_B(x)$ are subsequently determined on the basis of the following relationship:

$$\hat{\rho}=H^{-1}\cdot\hat{\mu}$$

from the linear attenuation coefficients $\mu_1(x)$ and $\mu_2(x)$, in which it holds true that $$\mu_1(x) = <\alpha_A>_{U_1} \cdot \rho_A(x) + <\alpha_B>_{U_1} \cdot \rho_B(x),$$

$$\mu_2(x) = <\alpha_A>_{U_2} \cdot \rho_A(x) + <\alpha_B>_{U_2} \cdot \rho_B(x),$$

$$a_{11} = <\alpha_A>_{U_1}, a_{12} = <\alpha_B>_{U_1},$$

$$a_{21} = <\alpha_A>_{U_2}, a_{22} = <\alpha_B>_{U_2},$$

$$H = \begin{pmatrix} a_{11} & a_{12} \\ a_{21} & a_{22} \end{pmatrix},$$

$$\hat{\mu} = \begin{pmatrix} \mu_1(x) \\ \mu_2(x) \end{pmatrix},$$

$$\hat{\rho} = \begin{pmatrix} \rho_A(x) \\ \rho_B(x) \end{pmatrix},$$

where:

$\mu_1(x)$ is the effective linear attenuation coefficient, assigned to the voxel x, relating to the voltage $U_1$, $\mu_2(x)$ is the effective linear attenuation coefficient, assigned to the voxel x, relating to the voltage $U_2$, $<\alpha_A>_{U_{1,2}}$ is the effective mass attenuation coefficient of the base material A in relation to the X-ray tube voltage $U_1$ and $U_2$, respectively, $<\alpha_B>_{U_{1,2}}$ is the effective mass attenuation coefficient of the base material B in relation to the X-ray tube voltage $U_1$ and $U_2$, respectively, and $\rho_{A,B}(x)$ is the density distribution of the base materials A and B respectively, in the voxel x.

Since the effective mass attenuation coefficients $<\alpha_j>_U$ for each substance j and for each voltage U, for which the tube spectrum is known, can in principle be calculated in advance, it is possible to determine in relation to each base material combination A, B given by density components the effective linear attenuation coefficient $<\mu>_U$ that would be yielded in the case of CT pictures with just this voltage U and subsequent CT reconstruction.

It holds that:

$$<\mu>_U=<\alpha_A>_U\rho_A+<\alpha_B>_U\rho_B, \quad (10)$$

the density components $\rho_A$ and $\rho_B$, respectively, being given by equation (9). It is therefore possible in step d) for the mass attenuation coefficients to be determined or appropriately provided in relation to the virtually prescribed voltage $U_3$.

The combination of equations (9) and (10) leads to the display of $<\mu>_U$ as a linear combination of the measured, reconstructed effective linear attenuation coefficients $\mu_1$ and $\mu_2$ (compare equations 1a and 1b), in accordance with the two voltages $U_1$ and $U_2$ used during dual energy CT recording:

$$<\mu>_U=\lambda_1(U,M_i)\cdot\mu_1+\lambda_2(U,M_i)\cdot\mu_2. \quad (11)$$

Note: if equation (11) is solved for $U=U_1$ and $U=U_2$ respectively, by successive substitution of (10), (9) and (5a) and (5b), respectively, the result is $\mu_1$ and $\mu_2$, respectively, as is fitting in terms of consistency.

The two weighting factors $\lambda_1$ and $\lambda_2$ of the linear combination in equation (11) depend only on the virtual X-ray tube voltage $U_3$ selected for the display, and on the two base material components $M_i$, that is to say on the two base material components assigned to the material class $M_i$. The computational outlay is thereby particularly low, since the weighting factors $\lambda_1$ and $\lambda_2$ in equation (11) are identical for all voxels that lie in the same material class.

The following relationship for the effective linear attenuation coefficient $\mu_3(x)$ being sought consequently results on considering, in the notation of equation (11), the spatial dependence of the voxel x, the material class $M_i$, and the virtual X-ray tube voltage $U_3$:

$$\mu_3(x)=\lambda_1(U_3,M_i)\cdot\mu_1(x)+\lambda_2(U_3,M_i)\cdot\mu_2(x). \quad (12)$$

In a further embodiment of the inventive method, the weighting factors $\lambda_1$ and $\lambda_2$ are therefore determined as weighting factors $\lambda_{1,2}(U_3,M_i)$ dependent on the virtual X-ray tube voltage $U_3$ and the material class $M_i$, or prescribed, and in step e) the image data are determined as third distribution of the linear attenuation coefficients $\mu_3(x)$ in accordance with the relationship:

$$\mu_3(x)=\lambda_1(U_3,M_i)\cdot\mu_1(x)+\lambda_2(U_3,M_i)\cdot\mu_2(x),$$

$\lambda_1$ and $\lambda_2$ being weighting factors dependent on $U_3$ and $M_i$, and $\lambda_1$ and $\lambda_2$ resulting from the combination of equations (9) and (10).

Since the gray scale values of the CT images are displayed as a rule in CT values (up to the scaling factor 1000), it is expedient to transform equation (12) by way of equation (2). It results in general in a linear combination and a constant that is indicated here by 0. In formal terms, it then holds for the CT values $C_3(x)$ being sought, which belong to the prescribed virtual voltage $U_3$ and to the material class $M_i$, that:

$$C_3(x_i)=k_0(U_3,M_i)+k_1(U_3,M_i)\cdot C_1(x)+k_2(U_3,M_i)\cdot C_2(x), \quad (13)$$

$C_1(x), C_2(x), C_3(x)$ being CT values belonging to the voltages $U_1, U_2$ and $U_3$, respectively, and $k_0(U_3,M_i), k_1(U_3,M_i), k_2(U_3,M_i)$ being constants resulting linearly from the weighting factors $\lambda_1(U_3,M_i), \lambda_2(U_3,M_i)$. Here, $C_1(x), C_2(x)$ correspond to the measured attenuation values contained in the first and second CT image data, respectively.

In a particularly preferred method embodiment variant, the weighting factors $\lambda_{1,2}(U_3,M_i)$ or the constants $k_0(U_3,M_i), k_1(U_3,M_i), k_2(U_3,M_i)$ for each material class $M_i$, and at least one X-ray tube voltage $U_3$ are prescribed and provided as a table. The first step in compiling this table is a numerical evaluation of equations (3a) and (3b) for the elements $a_{11}, a_{12}, a_{21}$ and $a_{22}$ in equations (5a) and (5b), respectively, of the matrix H in equation (6), and for the coefficients $<\alpha_A>_U$ and $<\alpha_B>_U$ in equation (10). For each desired virtual voltage $U_3$ and for each material class $M_i$ the table respectively contains the weighting factors $\lambda_{1,2}(U_3,M_i)$ or the constants $k_0(U_3,M_i), k_1(U_3,M_i), k_2(U_3,M_i)$.

Because of the lower quantum yield of the X-ray tubes at a low X-ray tube voltage, it happens that the data are recorded with a larger focal spot than given a higher voltage. In this case, the spatial resolution of the first and second CT image data would differ. The differences, owing to the focal spot, in the spatial resolution can, however, be matched to one another by suitable convolution kernels during the CT reconstruction or by 2-dimensional frequency filtering after the CT reconstruction. Consequently, it is possible when the CT image data are mixed in accordance with equations (12) and (13) for the spatial resolution to correspond to the spatial resolution as is normal in real standard CT pictures with the selected (here: virtual) voltage $U_3$.

When the inventive method is applied to the decomposition Method 2 (photo effect/Compton effect decomposition), only the variables $\rho_1$ and $\rho_2$ in equations (4a), (4b), (9) and (10) must be reinterpreted instead of material densities as photo effect and/or Compton effect components. The importance of the elements of the transformation matrix H changes correspondingly. Equation (11) is maintained mutatis mutandis, that is to say the weights can be calculated in advance. A simplification results to the extent that no further dependence on material class occurs as in equation (12). That is to say: all that is still required for each virtual voltage value $U_3$ are two and three, respectively, constant weights that can be calculated in advance on the basis of equations (3a), (3b).

In principle, at least one embodiment of the inventive idea described can also be transferred to the decomposition Method 3 ($\rho$-Z decomposition). The variables $\rho_A$ and $\rho_B$ must be reinterpreted by $\rho$ and Z, respectively, and the system of linear equations (4a), (4b) is replaced by a nonlinear relationship such as may be taken, for example, from B. J. Heismann et al., "Density and atomic number measurements with spectral X-ray absorption methods", J. Applied Physics, Vol 94(3), 2073-2079, (2003), the entire contents of which are hereby incorporated herein by reference. This dictates that the matrix $H^{-1}$ be interpreted as a nonlinear operator. The generally nonlinear generalization of equation (11) is decisive for the implementation. Finally, what is involved here is that each pair of CT values ($C_1$, $C_2$ and $\mu_1$, $\mu_2$, respectively) from the first and second CT image data is to be assigned a new CT value ($C_{U_3}$ and $\mu_{U_3}$, respectively) belonging to the virtual X-ray tube voltage $U_3$. This can be implemented for a prescribed value $U_3$ by accessing a two-parameter table calculated in advance with the aid of additional interpolation.

At least one embodiment of the inventive method has at least one of the following advantages:

For each arbitrarily prescribable virtual tube voltage $U_3$ it is possible to produce a third distribution of attenuation values from the provided first and second CT image data, and thus to produce a virtual CT image based thereon that relates to the X-ray tube voltage $U_3$.

At least one embodiment of the inventive method considers the radiometric nonlinear dependence of the attenuation coefficients and CT values on the X-ray tube voltage.

At least one embodiment of the method is adaptive according to the extent that the weighting factors are determined as a function of location and with consideration of the material classification.

The computational outlay is low, since the weighting factors are identical for all voxels in the same material class.

BRIEF DESCRIPTION OF THE DRAWINGS

Further advantageous refinements of embodiments of the invention are to be gathered from the following schematic drawing, in which:

FIG. 1 Flowchart of an embodiment of the inventive method.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows an embodiment of the inventive method for generating image data relating to a virtually prescribable X-ray tube voltage $U_3$ from first and second CT image data, wherein the first and second CT image data have been obtained by means of a computer tomograph by simultaneously or nearly simultaneously recording an object volume, the first CT image data describe a first distribution of the linear attenuation coefficient $\mu_1(x)$ for a first X-ray spectrum $S_1$, and the second CT image data describe a second distribution of the linear attenuation coefficient $\mu_2(x)$ for a second X-ray spectrum $S_2$, each voxel x of an object volume which is reconstructed from the first and second CT image data respectively being assigned the linear attenuation coefficients $\mu_1(x)$ and $\mu_2(x)$, and the first X-ray spectrum $S_1$ is assigned to a first X-ray tube voltage $U_1$, and the second X-ray spectrum $S_2$ is assigned to a second X-ray tube voltage $U_2$, in which case $U_1 \neq U_2$. The first and second CT image data are provided in step 101. The virtual X-ray tube voltage $U_3$, where $U_3 \neq U_1$ and $U_3 \neq U_2$, is prescribed in step 102. Using the first and second CT image data for two prescribable base materials A, B, step 103 determines in each case a spatial density distribution $\rho_A(x)$, $\rho_B(x)$, assigned to the base materials A, B, in the reconstructed object volume, $\rho(x)=\rho_A(x)+\rho_B(x)$ holding true for a density $\rho(x)$ of a voxel x in the reconstructed object volume. An effective mass attenuation coefficient $<\alpha_A>_{U_3}$ is provided in step 104 for the base material A, and an effective mass attenuation coefficient $<\alpha_B>_{U_3}$ is provided for the base material B, the effective mass attenuation coefficients $<\alpha_A>_{U_3}$ and $<\alpha_B>_{U_3}$ being valid respectively for an X-ray spectrum $U_3$ assigned to the virtual X-ray tube voltage $U_3$. The image data are determined in step 105 as a third distribution of linear attenuation coefficients $\mu_3(x)$ in the reconstructed object volume on the basis of the following relationship:

$$\mu_3(x) = <\alpha_A>_{U_3} \cdot \rho_A(x) + <\alpha_B>_{U_3} \cdot \rho_B(x).$$

A visual display of the image data determined in step 105 is performed in the last step 106.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks.

Examples of the removable medium include, but are not limited to, optical storage media such as CD-ROMs and DVDS; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for generating image data relating to a virtually prescribable X-ray tube voltage $U_3$ from first and second CT image data, wherein the first and second CT image data have been obtained by way of a computer tomograph by simultaneously, or nearly simultaneously, recording an object volume, the first CT image data describe a first distribution of the linear attenuation coefficient $\mu_1(x)$ for a first X-ray spectrum $S_1$, and the second CT image data describe a second distribution of the linear attenuation coefficient $\mu_2(x)$ for a second X-ray spectrum $S_2$, each voxel x of an object volume which is reconstructed from the first and second CT image data respectively being assigned the linear attenuation coefficients $\mu_1(x)$ and $\mu_2(x)$, and the first X-ray spectrum $S_1$ is assigned to a first X-ray tube voltage $U_1$, and the second X-ray spectrum $S_2$ is assigned to a second X-ray tube voltage $U_2$, in which case $U_1 \neq U_2$, the method comprising:

a) providing the first and second CT image data, b) prescribing the virtual X-ray tube voltage $U_3$, where $U_3 \neq U_1$ and $U_3 \neq U_2$, c) using the first and second CT image data for two prescribable base materials A, B to determine in each case a spatial density distribution $\rho_A(x)$, $\rho_B(x)$ assigned to the base materials A, B, in the reconstructed object volume, $\rho(x) = \rho_A(x) + \rho_B(x)$ holding true for a density $\rho(x)$ of a voxel x in the reconstructed object volume, d) providing an effective mass attenuation coefficient $<\alpha_A>_{U_3}$ for the base material A, and an effective mass attenuation coefficient $<\alpha_B>_{U_3}$ for the base material B, the effective mass attenuation coefficients $<\alpha_A>_{U_3}$ and $<\alpha_B>_{U_3}$ respectively being valid for an X-ray spectrum $S_3$ assigned to the virtual X-ray tube voltage $U_3$, and e) determining the image data as a third distribution of effective linear attenuation coefficients $\mu_3(x)$ in the reconstructed object volume in relation to the voltage $U_3$ on the basis of the following relationship:

$\mu_3(x) = <\alpha_A>_{U_3} \cdot \rho_A(x) + <\alpha_B>_{U_3} \cdot \rho_B(x)$.

2. The method as claimed in claim 1, wherein in step c) effective mass attenuation coefficients $<\alpha_A>_{U_1}$ and $<\alpha_A>_{U_2}$ are determined or provided for the base material A, and $<\alpha_B>_{U_1}$ and $<\alpha_B>_{U_2}$ are determined or provided for the base material B, the mass attenuation coefficients $<\alpha_A>_{U_1}$ and $<\alpha_B>_{U_1}$ being valid respectively for the X-ray spectrum $S_1$ assigned to the first X-ray tube voltage $U_1$, and the mass attenuation coefficients $<\alpha_A>_{U_2}$ and $<\alpha_B>_{U_2}$ respectively being valid for the X-ray spectrum $S_2$ assigned to the second X-ray tube voltage $U_2$, and in that in step c) the density distributions $\rho_A(x)$ and $\rho_B(x)$ are determined on the basis of the following relationship $\hat{\rho} = H^{-1} \cdot \hat{\mu}$ from the linear attenuation coefficients $\mu_1(x)$ and $\mu_2(x)$, in which it holds true that:

$\mu_1(x) = <\alpha_A>_{U_1} \cdot \rho_A(x) + <\alpha_B>_{U_1} \cdot \rho_B(x)$, $\mu_2(x) = <\alpha_A>_{U_2} \cdot \rho_A(x) + <\alpha_B>_{U_2} \cdot \rho_B(x)$, $a_{11} = <\alpha_A>_{U_1}, a_{12} = <\alpha_B>_{U_1}$, $a_{21} = <\alpha_A>_{U_2}, a_{22} = <\alpha_B>_{U_2}$, -continued $H = \begin{pmatrix} a_{11} & a_{12} \\ a_{21} & a_{22} \end{pmatrix}$, $\hat{\mu} = \begin{pmatrix} \mu_1(x) \\ \mu_2(x) \end{pmatrix}$, $\hat{\rho} = \begin{pmatrix} \rho_A(x) \\ \rho_B(x) \end{pmatrix}$, where:

$\mu_1(x)$ is the effective linear attenuation coefficient relating to the voltage $U_1$, $\mu_2(x)$ is the effective linear attenuation coefficient relating to the voltage $U_2$, $<\alpha_A>_{U_{1,2}}$ is the effective mass attenuation coefficient of the base material A in relation to the X-ray tube voltage $U_1$ and $U_2$, respectively, $<\alpha_B>_{U_{1,2}}$ is the effective mass attenuation coefficient of the base material B in relation to the X-ray tube voltage $U_1$ and $U_2$, respectively, and $\rho_{A,B}(x)$ is the density distribution of the base materials A and B respectively, in the voxel x.

3. The method as claimed in claim 1, wherein effective mass attenuation coefficients $<\alpha_A>_U$ and $<\alpha_B>_U$ for the base materials A, B, and an X-ray spectrum $S(E,U)$ assigned to an X-ray tube voltage U, in particular $U=U_1$, $U=U_2$, $U=U_3$, are determined as follows:

$<\alpha_{A,B}>_U = \int_0^{eU} \alpha_{A,B}(E) S(E, U) \, dE$, wherein $S(E, U) = \dfrac{F(E) Q(E) D(E) e^{-\mu_0(E) t}}{\int_0^{eU} F(E) Q(E) D(E) e^{-\mu_0(E) t} \, dE}$, where:

S(E,U) is a probability distribution density function normalized to 1,

U is the X-ray tube voltage, e is the elementary charge of an electron,

E is energy,

F(E) is the transparency of spectral filters which are present, which is dependent on the energy E, Q(E) is the energy-dependent emission photon spectrum of the X-ray tubes, D(E) is the response sensitivity, dependent on the energy E, of an X-ray detector, $\mu_0$ is the mean attenuation coefficient of the base material A and B, respectively, t is the mean material thickness of the base material A and B, respectively.

4. The method as claimed in claim 1, wherein a number N of different material classes $M_i$ (i=1, ..., N) are defined, each material class $M_i$ being determined by a prescribable combination of the base materials $A_i$ and $B_i$, and wherein, after step c) and before step e), voxels x in the reconstructed object volume, which exhibit the combination of the base materials $A_i$ and $B_i$, are assigned to the material class $M_i$.

5. The method as claimed in claim 4, wherein, in step e), the image data are determined as third distribution of the linear attenuation coefficients $\mu_3(x)$ according to:

$\mu_3(x) = \lambda_1(U_3, M_i) \cdot \mu_1(x) + \lambda_2(U_3, M_i) \cdot \mu_2(x)$, $\lambda_1$ and $\lambda_2$ being prescribed as weighting factors dependent on the virtual X-ray tube voltage $U_3$ and the material class $M_i$, and $\lambda_1$ and $\lambda_2$ being determined from a combination of the relationships $$\hat{\rho} = H^{-1} \cdot \hat{\mu} \text{ and } \mu_3(x) = \langle\alpha_A\rangle_{U_3} \cdot \rho_{A_i}(x) + \langle\alpha_B\rangle_{U_3} \cdot \rho_{B_i}(x).$$

6. The method as claimed in claim 5, wherein, in step e), the image data are determined as third distribution of the linear attenuation coefficients $\mu_3(x)$ by deriving the weighted sum:

$$\mu_3(x) = \lambda_1(U_3, M_i) \cdot \mu_1(x) + \lambda_2(U_3, M_i) \cdot \mu_2(x)$$

for in each case all voxels x of a material class $M_i$ and all material classes $M_i$.

7. The method as claimed in claim 1, wherein the virtual X-ray tube voltage $U_3$ is selected in such a way that $U_3$ lies between $U_1$ and $U_2$.

8. The method as claimed in claim 1, wherein $U_3$ corresponds to an X-ray tube voltage of approximately 120 kV.

9. The method as claimed in claim 5, wherein, in the first and second CT image data, the distributions of the linear attenuation coefficients $\mu_k(x)$ with k=1, 2 are present as attenuation values $C_k(x)$ in Hounsfield Units [HU], and wherein, in step e), a weighted sum is derived in accordance with $$C_3(x_i) = \kappa_0(U_3, M_i) + \kappa_1(U_3, M_i) \cdot C_1(x) + \kappa_2(U_3, M_i) \cdot C_2(x),$$

for all voxels x of a material class $M_i$ and all material classes $M_i$, where:
 $C_3(x)$ are attenuation values $C_3(x)$ in Hounsfield Units [HU] in relation to the X-ray tube voltage $U_3$, and
 $k_0(U_3, M_i), k_1(U_3, M_i), k_2(U_3, M_i)$ are constants dependent on $U_3$ and $M_i$,
 $k_0(U_3, M_i), k_1(U_3, M_i), k_2(U_3, M_i)$ being determined from a combination of the relationships:

$$\mu_3(x) = \lambda_1(U_3, M_i) \cdot \mu_1(x) + \lambda_2(U_3, M_i) \cdot \mu_2(x)$$

and $$C_k = \frac{\Delta\mu_k}{\mu_{k,W}} = \frac{\mu_k}{\mu_{k,W}} - 1; k = 1, 2.$$

10. The method as claimed in claim 5, wherein the weighting factors $\lambda_{1,2}(U_3, M_i)$ or the constants $k_0(U_3, M_i), k_1(U_3, M_i), k_2(U_3, M_i)$ for each material class $M_i$ and at least one X-ray tube voltage $U_3$ are prescribed as a table.

11. The method as claimed in claim 1, wherein a visual display of the determined image data $\mu_3(x)$ is performed in a step f) after step e).

12. The method as claimed in claim 2, wherein effective mass attenuation coefficients $\langle\alpha_A\rangle_U$ and $\langle\alpha_B\rangle_U$ for the base materials A, B, and an X-ray spectrum S(E,U) assigned to an X-ray tube voltage U, in particular $U=U_1$, $U=U_2$, $U=U_3$, are determined as follows:

$$\langle\alpha_{A,B}\rangle_U = \int_0^{eU} \alpha_{A,B}(E) S(E, U) dE,$$

wherein $$S(E, U) = \frac{F(E)Q(E)D(E)e^{-\mu_0(E)t}}{\int_0^{eU} F(E)Q(E)D(E)e^{-\mu_0(E)t} dE},$$

where:
 S(E,U) is a probability distribution density function normalized to 1,
 U is the X-ray tube voltage,
 e is the elementary charge of an electron,
 E is energy,
 F(E) is the transparency of spectral filters which are present, which is dependent on the energy E,
 Q(E) is the energy-dependent emission photon spectrum of the X-ray tubes,
 D(E) is the response sensitivity, dependent on the energy E, of an X-ray detector,
 $\mu_0$ is the mean attenuation coefficient of the base material A and B, respectively,
 t is the mean material thickness of the base material A and B, respectively.

13. The method as claimed in claim 2, wherein a number N of different material classes $M_i$ (i=1, ..., N) are defined, each material class $M_i$ being determined by a prescribable combination of the base materials $A_i$ and $B_i$, and
wherein, after step c) and before step e), voxels x in the reconstructed object volume, which exhibit the combination of the base materials $A_i$ and $B_i$, are assigned to the material class $M_i$.

14. The method as claimed in claim 2, wherein the virtual X-ray tube voltage $U_3$ is selected in such a way that $U_3$ lies between $U_1$ and $U_2$.

15. The method as claimed in claim 2, wherein $U_3$ corresponds to an X-ray tube voltage of approximately 120 kV.

16. The method as claimed in claim 8, wherein, in the first and second CT image data, the distributions of the linear attenuation coefficients $\mu_k(x)$ with k=1, 2 are present as attenuation values $C_k(x)$ in Hounsfield Units [HU], and wherein, in step e), a weighted sum is derived in accordance with $$C_3(x_i) = \kappa_0(U_3, M_i) + \kappa_1(U_3, M_i) \cdot C_1(x) + \kappa_2(U_3, M_i) \cdot C_2(x),$$

for all voxels x of a material class $M_i$ and all material classes $M_i$, where:
 $C_3(x)$ are attenuation values $C_3(x)$ in Hounsfield Units [HU] in relation to the X-ray tube voltage $U_3$, and
 $k_0(U_3, M_i), k_1(U_3, M_i), k_2(U_3, M_i)$ are constants dependent on $U_3$ and $M_i$,
 $k_0(U_3, M_i), k_1(U_3, M_i), k_2(U_3, M_i)$ being determined from a combination of the relationships:

$$\mu_3(x) = \lambda_1(U_3, M_i) \cdot \mu_1(x) + \lambda_2(U_3, M_i) \cdot \mu_2(x)$$

and $$C_k = \frac{\Delta\mu_k}{\mu_{k,W}} = \frac{\mu_k}{\mu_{k,W}} - 1; k = 1, 2.$$

17. The method as claimed in claim 15, wherein, in the first and second CT image data, the distributions of the linear attenuation coefficients $\mu_k(x)$ with k=1, 2 are present as attenuation values $C_k(x)$ in Hounsfield Units [HU], and wherein, in step e), a weighted sum is derived in accordance with $$C_3(x_i) = \kappa_0(U_3, M_i) + \kappa_1(U_3, M_i) \cdot C_1(x) + \kappa_2(U_3, M_i) \cdot C_2(x),$$

for all voxels x of a material class $M_i$ and all material classes $M_i$, where:
 $C_3(x)$ are attenuation values $C_3(x)$ in Hounsfield Units [HU] in relation to the X-ray tube voltage $U_3$, and
 $k_0(U_3, M_i), k_1(U_3, M_i), k_2(U_3, M_i)$ are constants dependent on $U_3$ and $M_i$,
 $k_0(U_3, M_i), k_1(U_3, M_i), k_2(U_3, M_i)$ being determined from a combination of the relationships:

$$\mu_3(x) = \lambda_1(U_3, M_i) \cdot \mu_1(x) + \lambda_2(U_3, M_i) \cdot \mu_2(x)$$

and $$C_k = \frac{\Delta \mu_k}{\mu_{k,W}} = \frac{\mu_k}{\mu_{k,W}} - 1; k = 1, 2.$$

18. The method as claimed in claim 9, wherein the weighting factors $\lambda_{1,2}(U_3, M_i)$ or the constants $k_0(U_3, M_i)$, $k_1(U_3, M_i)$, $k_2(U_3, M_i)$ for each material class $M_i$ and at least one X-ray tube voltage $U_3$ are prescribed as a table.

19. The method as claimed in claim 16, wherein the weighting factors $\lambda_{1,2}(U_3, M_i)$ or the constants $k_0(U_3, M_i)$, $k_1(U_3, M_i)$, $k_2(U_3, M_i)$ for each material class $M_i$ and at least one X-ray tube voltage $U_3$ are prescribed as a table.

20. The method as claimed in claim 17, wherein the weighting factors $\lambda_{1,2}(U_3, M_i)$ or the constants $k_0(U_3, M_i)$, $k_1(U_3, M_i)$, $k_2(U_3, M_i)$ for each material class $M_i$ and at least one X-ray tube voltage $U_3$ are prescribed as a table.

* * * * *